United States Patent [19]

Yoshikumi et al.

[11] Patent Number: 4,504,487
[45] Date of Patent: Mar. 12, 1985

[54] PLATINUM COMPOUND AND DRUG

[75] Inventors: Chikao Yoshikumi, Kunitachi; Takayoshi Fujii, Tokyo; Kenichi Saito, Tokyo; Masahiko Fujii, Tokyo; Koichi Niimura, Sayama, all of Japan

[73] Assignee: Kureha Kagaku Kogyo Kabushiki Kaisha, Tokyo, Japan

[21] Appl. No.: 431,374

[22] Filed: Sep. 30, 1982

Related U.S. Application Data

[62] Division of Ser. No. 265,838, May 21, 1981, Pat. No. 4,372,890.

[30] Foreign Application Priority Data

Jun. 11, 1980 [JP] Japan .................................. 55-78783

[51] Int. Cl.$^3$ .............................................. A61K 31/28
[52] U.S. Cl. .................................................... 514/492
[58] Field of Search ........................................... 424/287

[56] References Cited

U.S. PATENT DOCUMENTS 4,053,587 10/1977 Davidson et al. .................. 424/131
4,115,418 9/1978 Gale et al. ....................... 260/429 R
4,140,707 2/1979 Cleare et al. ..................... 260/429 R
4,177,263 12/1979 Rosenberg et al. ................ 424/131
4,203,912 5/1980 Hydes et al. ..................... 260/429 R
4,225,529 9/1980 Hydes et al. ..................... 260/429 R
4,228,090 10/1980 Hydes et al. ..................... 260/429 R

FOREIGN PATENT DOCUMENTS 2021946 12/1979 United Kingdom ................ 424/131

OTHER PUBLICATIONS

Chemical Abstracts, vol. 92, 1980, No. 99598K (p. 348).

Primary Examiner—Jerome D. Goldberg
Attorney, Agent, or Firm—Oblon, Fisher, Spivak, McClelland & Maier

[57] ABSTRACT

The present invention relates to a platinum compound having the formula

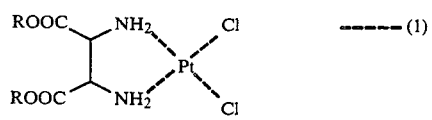

—————(1)

wherein R represents hydrogen atom, an alkali metal atom or a lower alkyl group. The platinum compound is effective as an antitumor and antimicrobial drug.

8 Claims, No Drawings

PLATINUM COMPOUND AND DRUG

This is a divisional of U.S. application Ser. No. 265,838, filed May 21, 1981, now U.S. Pat. 4,372,890.

BACKGROUND OF THE INVENTION

1. Field of the Invention

The present invention relates to a platinum compound having the formula

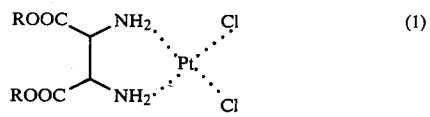

wherein R represents hydrogen atom, an alkali metal atom or a lower alkyl group and a drug comprising the same.

2. Description of the Prior Arts

Antitumor effects of platinum compounds have been studied to expect clinical applications. For example, cis-]diamine dichloroplatinum (II)] (hereinafter referring to as cis-ddp) has been proposed. The cis-ddp is water insoluble and has kidney toxicity and accordingly, the administration is limited. Various studies for overcoming the disadvantage have been made as disclosed in J. NATL. CANCER Inst. 57 841–845 (1976); Gann 69, 263–265 (1978). It has not been satisfactory to impart water solubility and to reduce kidney toxicity.

Various studies have been made to overcome these disadvantages.

SUMMARY OF THE INVENTION

It is an object of the present invention to provide novel platinum compounds having antimicrobial effects. The present compounds were also shown to have antitumor effects in mice and rabbits.

The novel platinum compounds of the present invention are compounds having the formula

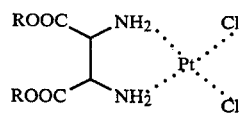

wherein R represents hydrogen atom, an alkali metal atom or a lower alkyl group.

DETAILED DESCRIPTION OF THE PREFERRED EMBODIMENTS

According to various studies for overcoming the disadvantages of the known platinum compounds, it has been found that platinum complexes having an amino acid derivative as ligand are effective. The present invention has been attained by the finding.

The novel platinum compound has a dimer of glycine as a ligand and one or two carboxyl groups thereof are converted into the ester or salt form to increase the solubility to water and to reduce the side-effect.

In the formula (1), R represents hydrogen atom, an alkali metal atom or a lower alkyl group. The lower alkyl group is methyl, ethy or propyl group and the alkali metal atom is sodium, potassium or lithium atom.

The process for producing the platinum compounds in this invention will be illustrated. A compound having the formula (2)

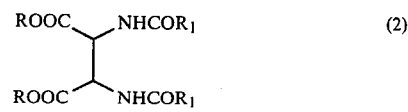

wherein R and $R_1$ respectively represent a lower alkyl group of methy, ethyl or propyl group (the known compound described in JCS: chem. comm. 238 (1977)) was dissolved in an alcohol such as methanol and ethanol and an acid such as hydrochloric acid and sulfuric acid is added to said solution to react them for 0.5 to 10 hours preferably 1 to 5 hours under refluxing. Then, the reaction mixture is concentrated under a reduced pressure and the product is recrystallyzed from an organic solvent such as a mixed solvent of methanol, ethanol, propanol, n-hexane and dioxane to obtain a compound (3).

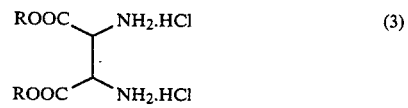

wherein R is defined in the formula (2). Then, the compound (3) is dissolved into water. A solution of a chloroplatinoate in water and a hydrogencarbonate are added to the solution of the compound (3).

The chloroplatinoate is sodium or potassium salt and the hydrogencarbonate is sodium, potassium, calcium or magnesium salt.

The reaction is performed at room temperature for 5 minutes to 3 hours and a precipitate is separated and dissolved into water and recrystallized. The resulting compound has the formula (4).

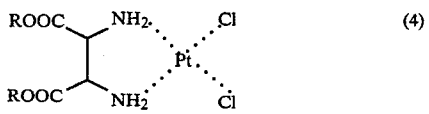

wherein R is defined in the formula (2).

The compound (4) is dispersed and dissolved in water and a metal hydroxide such as sodium or potassium hydroxide is added at an equimole and the mixture is heated at 60° to 100° C. for 10 to 180 minutes to react them. A water soluble organic solvent such as acetone, dioxane and DMSO is added to the reaction mixture to obtain a precipitate. The resulting precipitate is sodium or potassium salt as the compound of the present invention.

The free carboxylic acid thereof can be obtained by adding an acidic aqueous solution such as an aqueous solution of hydrochloric acid (pH: 1 to 4).

The characteristics of the resulting compounds are shown in Table 1.

TABLE 1

| No. | Compound | Melting point (°C.) | Solubility to water | C (%) | H (%) | N (%) | Note |
|---|---|---|---|---|---|---|---|
| 1 | $CH_3OOC$-CH($NH_2$)-CH($NH_2$)-$COOCH_3$ · Pt · $Cl_2$ | decompositon at about 253° C. | Δ | 16.30 (16.29 | 2.60 2.73 | 6.20 6.33) | Invention |
| 2 | $HOOC$-CH($NH_2$)-CH($NH_2$)-$COOH$ · Pt · $Cl_2$ | decompositon at about 250° C. | ○ | 11.40 (11.59 | 1.85 1.94 | 6.66 6.75) | " |
| 3 | $NaOOC$-CH($NH_2$)-CH($NH_2$)-$COONa$ · Pt · $Cl_2$ | brown coloring at about 265° C. | ◎ | 10.45 (10.53 | 1.31 1.32 | 6.10 6.13) | " |
| 4 | $KOOC$-CH($NH_2$)-CH($NH_2$)-$COOK$ · Pt · $Cl_2$ | brown coloring at about 270° C. | ◎ | 9.90 (9.79 | 1.30 1.23 | 5.75 5.70) | " |
| 5 | $NH_3$-Pt-$Cl_2$-$NH_3$ | trans-salt formation at 275° C. decomposition at 340° C. | X | | | | Reference |

Note:
◎ remarkably soluble
○ soluble
Δ soluble at high temperature
X insoluble

The acute toxicity of the compounds of the present invention will be illustrated.

Acute toxicity of the compounds is studied by an administration by route of intraperitoneal injection for ICR-JCL mice.

A solution of the compound in a physiological saline solution is administrated to the mice and the toxicity is observed after the administration to study mortal number for 7 days and lethal dosage ($LD_{50}$) is measured by Litchfield-Wilcoxon graph method.

$LD_{50}$ of Compound No. 5 as the reference compound is 50 mg./kg. whereas $LD_{50}$ of Compounds Nos. 1 to 4 as the compounds of the invention is more than 130 mg./kg. The lower toxicity of the compounds of the present invention is found. The compounds of the present invention have antimicrobial effects. These compounds have also been shown to have antitumor effects on mice and rabbits. The compounds of the invention have antimicrobial effects to gram's stain negative bacillius such as coliform bacillius and are effective for remedy from infection and especially effective as antimicrobial drug.

The drug is administered as a desired composition for oral or parenteral administration. The formulations of the drug compositions can be tablet, sugar coated tablet, pill, capsule, powder, granule, troche, liquid, suppository and injection. The drug is prepared by admixing the compound with a pharmacologically acceptable carrier. Suitable carriers include sugar, glucose, sorbitol, mannitol, potatostarch, cornstarch, amylopectin, and other starches; cellulose derivatives such as carboxymethyl cellulose, hydroxypropyl cellulose; gelatin, magnesium stearate, polyvinyl alcohol, calcium stearate, polyethyleneglycol, arabic gum, talc, titanium dioxide; vegetable oils such as olive oil, peanut oil and sesame oil; paraffin oil, neutral fats, ethanol, normal saline solution, sterilized water, glycerin, coloring agents, seasonings, thickeners, stabilizers, surfactants and buffers and other pharmacologically acceptable carriers. The drug may comprises 0.001 to 85 wt. % especially 0.005 to 60 wt. % of the compound of the invention. The dose of the compound of the invention is ranging from 0.005 to 100 mg. preferably 0.01 to 50 mg./kg./day/adult depending upon the condition.

The present invention will be further illustrated by certain examples and references which are provided for purposes of illustration only.

EXAMPLE 1

Into 80 ml. of methanol, 2,000 mg. of dimer of methyl ester of N-acetyl glycine was dissolved and about 1 ml. of hydrochloric acid was added and the mixture was refluxed for 3 hours.

After the reaction, the reaction mixture was concentrated under a reduced pressure and the product was recrystallized from a mixture of ethanol and n-hexane to obtain 1.5 g. of the compound having the formula (3) wherein R is methyl group. The yield was 78%. The product had a melting point of 158° to 159° C. and the following elementary analysis.

|  | C (%) | H (%) | N (%) |
|---|---|---|---|
| Calculated: | 28.92 | 5.65 | 11.23 |
| Found: | 29.10 | 5.60 | 11.00 |

The product was soluble in water, methanol and ethanol and insoluble in benzene and chloroform. The Infrared spectrum is shown in Table 6-1.

EXAMPLE 2

Into 1 ml. of water, 400 mg. of the compound obtained by Example 1 was dissolved and a solution of 540 mg. of potassium chloroplatinoate in 2 ml. of water was added and 108 mg. of $NaHCO_3$ as powder was gradually added. The precipitated crystal was separated and recrystallized from water to obtain 4 mg. of powdery crystal. The product was soluble in hot water of 60° C. and insoluble in organic solvents. The yield was 56%. The product had a melting point of 253° C.(decomposition) and had the following elementary analysis:

|  | C (%) | H (%) | N (%) |
| --- | --- | --- | --- |
| Calculated: | 16.29 | 2.73 | 6.33 |
| Found: | 16.30 | 2.60 | 6.20 |

The product had the formula (4) wherein R is methyl group. The infrared spectrum is shown in Table 6-2.

EXAMPLE 3

To 10 ml. of water, 200 mg. of the product of Example 2 and sodium hydroxide at an equimolar ratio were added and the mixture was stirred at 80° C. for 30 minutes. After cooling the mixture, acetone was added to separate a precipitate. The precipitate was dried to obtain a powder. The yield was 53%. The product had a melting point of 265° C. (decomposition). The product was soluble in water and insoluble in organic solvents of benzene and chloroform. The infrared spectrum is shown in Table 6-3. The product had the formula (4) wherein R is Na.

In accordance with the same process except using potassium hydroxide instead of sodium hydroxide, the product of the present invention as the potassium salt was obtained. The product had a melting point of 270° C. (decomposition). The yield was 55%. The infrared spectrum is shown in Table 6-4. The product had the formula (4) wherein R is K.

EXAMPLE 4

Into 5 ml. of water, 100 mg. of the product of Example 3 as the sodium salt was dissolved and hydrochloric acid was added to give pH of 2 to 3 to precipitate the crystal. The yield was 45%. The product had a melting point of 250° C. (decomposition) and was soluble in water. The product had the formula (4) wherein R is H.

EXAMPLE 5

Antitumor effects of the products to mouse P-388 leukemia were tested.

P-388 ascites cells obtained by a successive cultivation in DBA/2 mice were transplanted by the route of intraperitoneal injection into $CDF_1$ mice (10 mice in one group) at a rate of $1 \times 10^6$/mouse. From 24 hours after the transplantation, a solution of each compound in physiological saline solution was injected once a day for 5 days as 5 times by the route of intraperitoneal injection. Each average survival days (T) of the administrated group and each average survival days (C) of control group were measured to calculate each percentage increase in life span (ILS(%))

$$ILS(\%) = T/C \times 100$$

TABLE 2

| No. | Compound | Dose (mg/kg) | ILS (%) | Note |
| --- | --- | --- | --- | --- |
| 1 | $CH_3OOC$–$C(NH_2)(NH_2)$–$COOCH_3$ · $Pt(Cl)(Cl)$ | 5 | 210 | Invention |
| 2 | $HOOC$–$C(NH_2)(NH_2)$–$COOH$ · $Pt(Cl)(Cl)$ | 5 | 220 | " |
| 3 | $NaOOC$–$C(NH_2)(NH_2)$–$COONa$ · $Pt(Cl)(Cl)$ | 5 | 230 | " |
| 4 | $KOOC$–$C(NH_2)(NH_2)$–$COOK$ · $Pt(Cl)(Cl)$ | 5 | 225 | " |
| 5 | $NH_3$–$Pt(Cl)(Cl)$–$NH_3$ | 5 | 180 | Reference (cis-ddp) |

As it is clear from the results, the compounds of the present invention impart higher ILS(%) than that of the reference cis-ddp. Moreover, the solubilities of the compounds of the present invention to water are increased to reduce kidney toxicity and other side-effects.

In the group for the administration of cis-ddp, remarkable weight decrease and kidney cell damage were observed for all of 10 mice. In the groups of the administration of the compounds of the present invention, slight weight decreases were found during the administration, however, the weight were recovered and kidney cell damages were remarkably slight.

EXAMPLE 6

Antitumor effect to rabbit V-7 tumor

A solid tumor obtained by transplantation and proliferation to rabbit femoralis was extracted and cut by scissors in pieces and scieved through a stainless steel screen (200 mesh). The tumor cell was transplanted into thin muscle of rabbit femoralis by the route of an injection at a rate of about $1.5 \times 10^7$ cells/0.4 ml. Each compound was administered for 2 times 7th and 11th day after the transplantation, and average survival days were measured with the control group and each life prolonging rate was calculated.

TABLE 3

| Compound | Dose (mg/kg) | Life prolonging rate (%) |
| --- | --- | --- |
| $NH_3$–$Pt(Cl)(Cl)$–$NH_3$ | 5 | 147 |

TABLE 3-continued

| Structure | Dose (mg/kg) | Life prolonging rate (%) |
|---|---|---|
| CH₃OOC-C(NH₂)-Pt(Cl)₂-C(NH₂)-COOCH₃ | 5 | 180 |
| NaOOC-C(NH₂)-Pt(Cl)₂-C(NH₂)-COONa | 5 | 200 |
| HOOC-C(NH₂)-Pt(Cl)₂-C(NH₂)-COOH | 5 | 193 |

Each side-effect and each solubility to water were tested.

In the tests, severe albuminuria as the indication of kidney toxicity was found in the control group whereas only slight albuminuria was found in the groups of the administrations of the compounds of the present invention.

The results of the observation of alubuminuria and the solubilities of the compounds are shown in Table 4.

The properties of the compound disclosed in the prior art are also compared. The improvement of solubilities to water and the reduction of kidney toxicity of the compound of the present invention are found.

TABLE 4

| | Structure | Solubility to water | Kidney toxicity albuminuria |
|---|---|---|---|
| Invention | CH₃OOC-C(NH₂)-Pt(Cl)₂-C(NH₂)-COOCH₃ | Δ | ++ |
| | HOOC-C(NH₂)-Pt(Cl)₂-C(NH₂)-COOH | ○ | + |
| | NaOOC-C(NH₂)-Pt(Cl)₂-C(NH₂)-COONa | ◎ | + |
| Reference | NH₃-Pt(Cl)₂-NH₃ (²) | X | +++ |
| | Cl-Pt(NH₂-cyclohexane-NH₂)-Cl (¹) | Δ | +++ |
| | Pt(D-glucuro)₂ (trans(l)-1,2-cyclohexanediamine)(²) | ○ | +++ |

Note:
◎ highly soluble
○ soluble
Δ soluble by heating insoluble matter at room temperature
X insoluble
+ albuminuria is found for 1 to 2 rabbits in one group of 10 rabbits.
(¹)Sandra J. Meischen, J. Natl. Cancer, Inst. 57 841 (1976)
(²)Y. Kidani Gann 69 263 (1978)

EXAMPLE 7

Antimicrobial effect (7-1) Each compound diluted as series of two times dilutions and each diluted solution was admixed with Heart infusion agar medium (Nippon Eiyo Kagaku K.K.) to prepare each plate for culture.

Escherichia coli strain was cultured in Trypto-soy bouillon at 37° C. for 17 hours and one platinum loop of the cultured coliform bacillius strain was put on each plate to culture it at 37° C. for 18 hours and each growth of the strain was observed.

TABLE 5

| | Structure | Reduction of coliform bacillius: Dilution times | | | | |
|---|---|---|---|---|---|---|
| Inv. | CH₃OOC-C(NH₂)-Pt(Cl)₂-C(NH₂)-COOCH₃ | -+ | - | - | - | - |
| | HOOC-C(NH₂)-Pt(Cl)₂-C(NH₂)-COOH | -+ | - | - | - | - |
| | NaOOC-C(NH₂)-Pt(Cl)₂-C(NH₂)-COONa | -++ | -+ | - | - | - |
| | KOOC-C(NH₂)-Pt(Cl)₂-C(NH₂)-COOK | -++ | -+ | - | - | - |
| Ref. | NH₃-Pt(Cl)₂-NH₃ | -+ | - | - | - | - |
| | Cl-Pt(NH₂-cyclohexane-NH₂)-Cl | -+ | - | = | - | |

Note:
+: growth inhibition of strain

In vitro tests, the antimicrobial effects of the compounds of the present invention were found.

(7-2) Since the compounds of the present invention had antimicrobial effects to coliform bacillius, the infection remedy tests of the compounds of the present invention were carried out.

Coliform bacillius strain was inoculated to mice by route of intraperitoneal injection at a rate of $1\times10^8$/mouse. Each compound was administrated at a dose of 1 mg. to 100 mg./kg. 1 to 3 hours after the injection by route of intraperitoneal injection or route of oral administration. During 7 days from the administration, the conditions of mice were observed to measure survival rates. The survival rates were higher than 50%.

The fact show that the compounds of the present invention are effective not only in vitro tests but also as chemotherapeutic drugs for test infections.

EXAMPLE 8

Compound No. 1: 50 g.
Lactose: 300 g.
Hydroxypropyl cellulose: 1.5 g.

The components were well mixed and the mixture was tabletted or the mixture was kneaded as granulated by passing through a screen of an extrusion type granulation machine and the granule was dried well and tabletted.

EXAMPLE 9

In each vial, 10 mg. of Compound No. 2 was charged in asepsis and moisture and bacteria were removed in closed condition. Before the administration, 5 ml. of 5% glucose solution for injection was charged to prepare an injection.

EXAMPLE 10

In each vial, 50 mg. of Compound No. 4 was charged in asepsis and moisture and bacteria were removed in closed condition. Before the administration, 5 ml. of 0.9% physiological saline solution was charged to prepare an injection.

TABLE 6

| Table 6-1 | | |
|---|---|---|
| 3300 cm$^{-1}$ (w) | 2840 cm$^{-1}$ (m) | 2620 cm$^{-1}$ (m) |
| 1760 cm$^{-1}$ (s) | 1749 cm$^{-1}$ (s) | 1590 cm$^{-1}$ (w) |
| 1528 cm$^{-1}$ (w) | 1500 cm$^{-1}$ (s) | 1430 cm$^{-1}$ (m) |
| 1365 cm$^{-1}$ (m) | 1291 cm$^{-1}$ (s) | 1225 cm$^{-1}$ (s) |
| 1140 cm$^{-1}$ (w) | 1070 cm$^{-1}$ (m) | 1040 cm$^{-1}$ (m) |
| 950 cm$^{-1}$ (m) | 878 cm$^{-1}$ | |
| Table 6-2 | | |
| 3440 cm$^{-1}$ (m) | 3240 cm$^{-1}$ (m) | 3100 cm$^{-1}$ (m) |
| 2960 cm$^{-1}$ (w) | 1740 cm$^{-1}$ (s) | 1570 cm$^{-1}$ (m) |
| 1430 cm$^{-1}$ (m) | 1390 cm$^{-1}$ (m) | 1300 cm$^{-1}$ (s) |
| 1250 cm$^{-1}$ (s) | 1095 cm$^{-1}$ (s) | 1015 cm$^{-1}$ (m) |
| Table 6-3 | | |
| 3440 cm$^{-1}$ (m) | 3280 cm$^{-1}$ (m) | 3240 cm$^{-1}$ (m) |
| 3100 cm$^{-1}$ (m) | 2960 cm$^{-1}$ (w) | 1700 cm$^{-1}$ (s) |
| 1580 cm$^{-1}$ (m) | 1430 cm$^{-1}$ (m) | 1395 cm$^{-1}$ (w) |
| 1305 cm$^{-1}$ (s) | 1260 cm$^{-1}$ (s) | 1240 cm$^{-1}$ (s) |
| 1100 cm$^{-1}$ (s) | 1020 cm$^{-1}$ (m) | |
| Table 6-4 | | |
| 3380 cm$^{-1}$ (m) | 1660 cm$^{-1}$ (m) | 1600 cm$^{-1}$ (s) |
| 1530 cm$^{-1}$ (m) | 1490 cm$^{-1}$ (m) | 1410 cm$^{-1}$ (m) |
| 1320 cm$^{-1}$ (m) | 1280 cm$^{-1}$ (s) | 1170 cm$^{-1}$ (s) |
| 840 cm$^{-1}$ (m) | | |

We claim:

1. A drug comprising 0.001–85 wt. % of the drug of a platinum compound having the formula

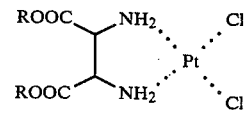

wherein R is hydrogen atom, an alkali metal atom or a lower alkyl group, as an active ingredient, and a pharmacologically acceptable carrier.

2. The drug according to claim 1 wherein said lower alkyl is methyl, ethyl or propyl group.

3. The drug according to claim 1 wherein R is methyl group.

4. The drug according to claim 1 wherein R is hydrogen atom.

5. The drug according to claim 1 wherein R is sodium atom.

6. The drug according to claim 1 wherein R is potassium atom.

7. The drug of claim 1, wherein the amount of the platinum compound is 0.005–60 wt %.

8. The drug of claim 1, wherein the carrier is selected from the group consisting of sugar, glucose, sorbitol, mannitol, potato starch, corn starch, amylopectin, carboxymethyl cellulose, hydroxypropyl cellulose, gelatin, magnesium stearate, polyvinyl alcohol, calcium stearate, polyethyleneglycol, arabic gum, talc, titanium dioxide, olive oil, peanut oil, sesame oil, paraffin oil, neutral fats, ethanol, normal saline solution, sterilized water, glycerin, coloring agents, seasonings, thickeners, stabilizers, surfactants and buffers.

* * * * *